(12) United States Patent
Pereira et al.

(10) Patent No.: US 9,896,358 B2
(45) Date of Patent: Feb. 20, 2018

(54) METHOD OF TREATING CELLULOSE CONTAINING WASTE WATER SLUDGE FOR THE MANUFACTURE OF LINERBOARD AND CELLULOSIC ETHANOL PRODUCTION

(71) Applicant: Solenis Technologies, L.P., Schaffhausen (CH)

(72) Inventors: Fabricio Saab Pereira, Araraquara-SP (BR); Adriano Marques Gomes, Araraquara-SP (BR)

(73) Assignee: SOLENIS TECHNOLOGIES, L.P., Schaffhausen (CH)

( * ) Notice: Subject to any disclaimer, the term of this patent is extended or adjusted under 35 U.S.C. 154(b) by 0 days.

(21) Appl. No.: 15/186,608

(22) Filed: Jun. 20, 2016

(65) Prior Publication Data

US 2017/0362106 A1    Dec. 21, 2017

(51) Int. Cl.
  *C07C 29/00* (2006.01)
  *C02F 1/68* (2006.01)
  *C02F 11/12* (2006.01)
  *D21C 11/00* (2006.01)
  *C02F 103/28* (2006.01)

(52) U.S. Cl.
  CPC ............... *C02F 1/68* (2013.01); *C02F 11/12* (2013.01); *C07C 29/00* (2013.01); *D21C 11/00* (2013.01); *C02F 2103/28* (2013.01)

(58) Field of Classification Search
  USPC ......................................................... 568/840
  See application file for complete search history.

(56) References Cited

PUBLICATIONS

Duet et al. "Environmental aspects of drug and chemical use in aquaculture: An overview" Opinions Mediterraneennes, 2009, 105-126.*

* cited by examiner

*Primary Examiner* — Clinton A Brooks
*Assistant Examiner* — Ana Z Muresan
(74) *Attorney, Agent, or Firm* — Michael J. Herman

(57) ABSTRACT

The current process relates to the treatment of a primary sludge that is produced from waste water treatment facilities such as a pulp mill or a pulp and paper mills. It further relates to a process of using the primary sludge in the production of cellulosic ethanol. It further relates to the use of the treated primary sludge in the manufacture of recycled linerboard.

19 Claims, 1 Drawing Sheet

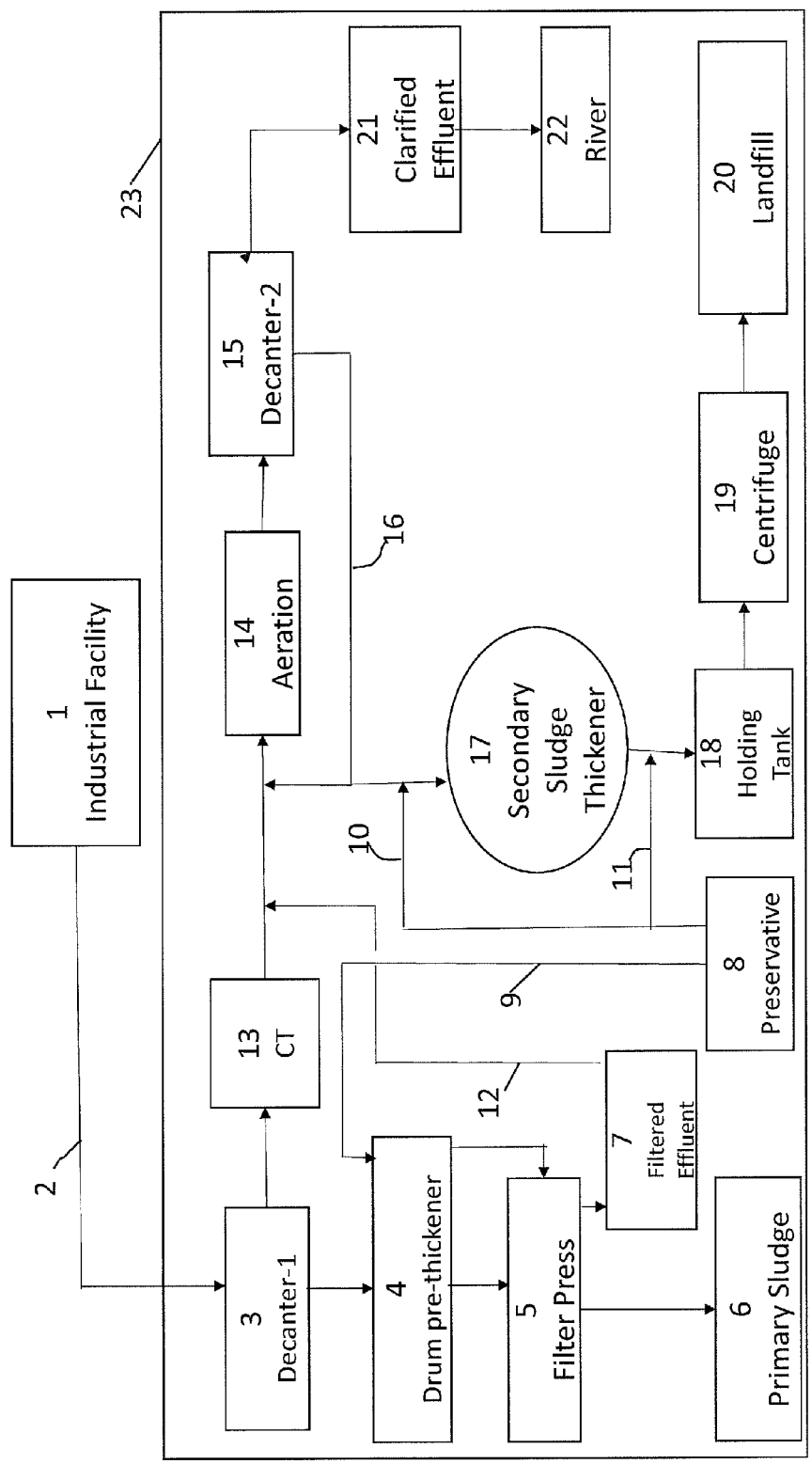

METHOD OF TREATING CELLULOSE CONTAINING WASTE WATER SLUDGE FOR THE MANUFACTURE OF LINERBOARD AND CELLULOSIC ETHANOL PRODUCTION

BACKGROUND

The present invention relates to the treatment of the primary sludge that is produced from waste water treatment facilities such as a pulp mill or a pulp and paper mill, wherein cellulose fibers are a significant portion of the solid waste. It further relates to a process of using the primary sludge resulting from the waste water in the production of cellulosic ethanol. It further relates to the use of the primary sludge in the manufacture of recycled linerboard.

The manufacture of paper involves blending, in water, a pulp material (generally cellulose fiber) with fillers, such as clay, and other additives to create a stock slurry mixture referred to herein as a pulp. The pulp is then processed through a papermaking machine to form a sheet. The water is then extracted from the sheet and the sheet is then pressed and dried, thereby forming a paper product. The extracted water or industrial effluent stream, contains an amount of waste solids, which is mostly fiber and filler material.

The industrial effluent stream containing these waste solids that cannot be directly recycled by, for example, paper mill "saveall" devices, are conveyed by the sewerage system to a waste water treatment plant facility. The industrial effluent stream goes through a series of operations depending on the particular set-up of the waste water treatment facility, to concentrate and dewater the waste solids producing a sludge. Ultimately, the industrial effluent stream is passed through a filter press, wherein the waste solids are concentrated into a primary sludge and the filtered waste water from the press is further processed in an aeration pond producing a secondary or bacteria activated sludge, containing biological waste and water that is fit for discharge or reuse.

However, the largest portion of this stream is the primary sludge produced from the waste water treatment plants. After dewatering, the solids are contained in a concentrated, typically 40%-60% solids sludge. The main components of this sludge are cellulosic fibers and filler material such as clays and silicates.

As mentioned above, the filtered water after separation from the primary sludge still contains dissolved or finely suspended organic matter which needs to be reduced in order for safe discharge. This stream is further treated in an activated sludge process and sent to an aeration pond. The secondary sludge which is the product of the biological process is usually disposed of in landfills. Some papermaking processes recycle primary sludge, however, in addition to issues with strength properties, paper sludge has been found to adversely affect sizing and cause size reversion.

"Sludge" is a generic term for the solid residue that results from pulp and papermaking. Sludge is typically produced at two steps in the process of treating the effluent water from the industrial facility. Primary sludge, containing most of the suspended solids in the effluent stream, is recovered by the first stage of the processing at the primary clarifier. Primary clarification is usually carried out by sedimentation or through a filter press, but can also be performed by dissolved air flotation. In sedimentation, the waste water to be treated is pumped into large settling tanks, with the solids being removed from the tank bottom. These solids can range from 1.5% to 6.5% depending on the characteristics of the material. The overflow, or clarified water, is passed on for secondary treatment.

If the industrial effluent is passed through a filter press the primary sludge is collected and the filtered effluent piped back into the process for secondary treatment.

The waste water resulting from the separation of the primary sludge usually contains dissolved organic materials as well as some portion of finely suspended solids. These need to be reduced or eliminated before the water stream can be safely discharged or reused. Secondary treatment is usually a biological process in which micro-organisms convert the waste to carbon dioxide and water while consuming oxygen. The resulting solids are then re-moved through clarification as in the primary treatment. The resulting secondary or biological sludge is sent to settling pond. In general, primary sludge is easier to dewater than the secondary or biological sludge resulting from the second stage. This secondary or biological sludge is typically sent to a landfill.

The paper industry currently uses several methods to dispose of the sludge that pulp and paper production generates, such as landspread in the summer when the fields are accessible and incinerate for steam production during the winter when steam demand is greater. Currently, most sludge produced by pulp mills or pulp and paper mills is dewatered and landfilled. These landfills can be industrial landfills that are constructed and operated by the mills or they can be independently owned, requiring the mills to pay a "tipping fee" for sludge disposal. Current landfills are reaching capacity and new ones are difficult to site and construct because of more stringent environmental requirements.

Some alternative processes, such as fluidized bed systems, seem to be more environmentally friendly. Microbiological treatment is still relatively new and is yet to be used on a large scale. Alternative uses for sludge ash, such as bricks and cement, are an excellent option if a user can be found near the mill and if long term contracts can be acquired. New products developed from pulp and paper mill sludge, however, need to have a market to make them economically feasible. It does not make sense to develop and create products for which there is no market.

Even though there are several applications where the cellulose fiber in the primary sludge can be used for economic benefit such as for ethanol production or for recycle cellulose products, the main impediment is that the fibers in the primary sludge are quickly degraded by biological agents present naturally in the system. This reduces the value of the fiber in the sludge. In order to mitigate the biodegradation of the fibers it is desirable to add a preservative to the effluent water prior to the separation. However, the preservative will also reside in the waste water after the separation process and thus reduce the potency of the biological agents in the secondary treatment step. Thus, it is desirable to have a preservative that will substantially reduce the biodegradation of the cellulose fibers in the primary sludgy without affecting the kinetics of COD reduction in the secondary biological treatment step of the waste water. While there have been attempts to treat the sludge using various compositions and processing techniques, there is still a need to find new processes and applications wherein the primary sludge can be used as a renewable source of new products, while maintaining the efficacy of the secondary treatment step

BRIEF SUMMARY OF THE INVENTION

Provided is a process of treating an industrial effluent or waste water stream containing cellulosic fibers and producing a primary sludge from the effluent stream for use in the production of cellulosic ethanol.

Also provided is a process of using the primary sludge in the manufacture of recycled linerboard or cardboard, which terms are used interchangeably hereinafter.

More particularly, the process involves adding a preservative comprising benzalkonium chloride; sodium hypochlorite; and oxitetracycline, to an industrial effluent stream, concentrating the waste solids effluent stream into a primary sludge and a filtered waste water that is further processed and clarified. The primary sludge can then be used in the production of cellulosic ethanol or the manufacture of recycled cardboard or linerboard.

Finally, provided is a process of treating an industrial effluent stream at a waste water treatment facility with a preservative wherein the bio-organic activity in an aeration or waste treatment pond of the waste water facility is unaffected.

BRIEF DESCRIPTION OF THE DRAWINGS

FIG. 1 shows a schematic of a typical waste water processing facility.

DETAILED DESCRIPTION OF THE INVENTION

The present process provides for the treatment of an industrial effluent stream at a waste water treatment facility, wherein the primary sludge that is produced can be used in the production of cellulosic ethanol. The process also allows for the primary sludge to be used in the manufacture of recycled cardboard or linerboard. The current process can be used in any industrial effluent stream that contains at least 20% by weight cellulosic fiber, such as those produced by a pulp mill or a pulp and paper mill.

In the current process, a preservative comprising a formulation of benzalkonium chloride; sodium hypochlorite; and oxitetracycline, is added to an industrial effluent stream prior to, or at the filter press producing the primary sludge or a combination thereof, at a waste water treatment plant. More particularly, the amount of benzalkonium chloride relative to the total actives can be from 40-75%, the amount of sodium hypochlorite can be from 8-20% and the amount of oxitetracycline can be from 0.1-1%. The effluent is filter pressed producing a primary sludge and a filtered waste water effluent stream. The primary sludge can then be used in the production of cellulosic ethanol or recycled cardboard. The filtered waste water effluent is further processed in a biological (activated sludge) process wherein the residual organic matter in the waste water is consumed by bioorganisms and clarified, further separating the biological waste solids from the waste water. The clarified waste water is discharged back into the environment and the waste solids returned to the aeration tank, to keep working as activated sludge. The excess of this sludge, goes to the sludge thickener and after for a centrifuge, producing a secondary or biological sludge that is usually sent to a landfill. The centrifugal wastewater can be returned to the aeration tank to be process again.

In a preferred process, referring to FIG. 1, an industrial effluent stream (2) is discharged from an industrial facility (1), to a waste water treatment facility (23). In this particular version, the industrial effluent stream goes through a first decanter (3), which begins to concentrate the waste solids. The waste water goes through additional processing such as a cooling tower (13), aeration pond where the microbiological organisms break down the organic material (14), a second decanter (15), a clarifier (21) and ultimately discharged, for example, into a river (22). In FIG. 1, the waste solids continue through a drum pre-thickener (4), these are mainly used for dewatering paper machine broke and pre-thickening reject pulp. The preservative (8) can be added anywhere in the system prior to the filter press or at the filter press of a combination thereof. In FIG. 1, the preservative (8) is added at the drum pre-thickener (4) and/or the press section (5). The filtered effluent (7) is piped back into the industrial effluent stream, for example after the cooling tower (13), for secondary processing.

The sludge resulting from the filter press is considered a primary sludge (6) and can have a consistency of from about 30% to about 60% solids, and wherein the fiber comprises at least about 20% by dry wt. of the sludge, can be about 35% fiber and may be about 45% fiber by dry wt. sludge.

The preservative (8) is a formulation that comprises benzalkonium chloride; sodium hypochlorite; and oxitetracycline. More particularly, the amount of benzalkonium chloride relative to the total actives can be from 40-75%, the amount of sodium hypochlorite can be from 8-20% and the amount of oxitetracycline can be from 0.1-1%. In FIG. 1, the preservative is added at the drum pre-thickener (4) and/or the filter press (5). However, it can be added at other locations prior to those places. The preservative can be added in an amount of from about 100 parts-per-million (ppm) to about 1000 ppm by dry wt. sludge.

The filtered effluent (7) in FIG. 1, is piped back into the system and mixed back in with the waste water coming from the first decanter (3) and cooling tower (13). The effluent continues through an aeration pond (14), which provides an effective means of removing the organic components and moving solids to create controlled mixing patterns, and through a second decanter (15). The second decanter (15) further separates the solid waste from the waste water creating a sludge that is further processed and a clarified effluent (21). The clarified effluent (21) is then discharged, for example, into a river (22).

The excess of this sludge that return to aeration tank (16) is further thickened (17) prior to being pumped into a holding tank (18), and after into a centrifuge, creating the secondary sludge. The secondary sludge can be optionally treated with preservative prior to being discharged into a landfill. FIG. 1, shows the optional preservative being added before and after the secondary sludge thickener (17). The optional preservative can be used to help keep bacterial counts at acceptable levels. Generally, when using the plating method, bacterial counts should not exceed 100,000.

An industrial waste facility can be configured in many different ways. For example, the filtered effluent (7), as well as effluent from the centrifuge (19), could be piped back into the system at an equalizer tank (not shown) prior to the cooling tower (13). From the cooling tower the effluent would go through the same process as described wherein the effluent goes through an aeration unit (14) followed by the second decanter (15) wherein the sludge is recycled (16) back to the aeration unit (14), with any excess sludge going to the secondary sludge thickener (17) and centrifuge (19) producing a secondary or activated sludge, which is generally sent to a landfill (20). The effluent from the centrifuge (19) can then be recycled back into the process before or after the cooling tower.

As mentioned above, the waste solids that are collected in the secondary sludge thickener (17), after the second decanter (15), can be optionally treated prior to, during, or after going through the secondary sludge thickener (17) or a combination thereof. In preferred embodiments, the dosage of the secondary sludge with the preservative can be from 0 to about 1,200 ppm.

The following examples further illustrate the current process, and they are not intended to be in any way limiting to the scope of the process as claimed.

EXAMPLES

Example 1

The following was performed to evaluate the efficiency of the preservative for the control of bacteria. Primary sludge samples were collected from a pulp and papermill wastewater, and analyzed by the plating method described below, with a culture medium means of culture PCA (Plate Count Agar) to the growth of total bacteria.

The cultivation plating or plating reveals the number of microorganisms able to multiply and form colonies in appropriate culture media and under suitable incubation conditions. Each colony developed is originating from a functioning unit.

Preparation of Samples

One hundred grams of primary sludge was added to two 200 ml Erlenmeyer flasks Sample 1 was of the primary sludge without using the preservative, and Sample 2 was of the primary sludge with 500 ppm of preservative. For each Erlenmeyer flask, six sterilized test tubes were prepared by adding 9 milliliter (ml) of distilled water to each test tube. One ml of the Sample 1 and 2, respectively was transferred to the first test tube. The first test tube is agitated and a 1 ml of sample was removed and put in the next or second test tube and agitated and a 1 mil sample taken from the second test tube and placed in a third test tube, and so on to the sixth tube.

Surface Plating Method—"Spread Plate"

We merged the medium (pass the material from a solid to a liquid phase) in an autoclave (this can also be done by microwave); the cast cultures for each of Sample 1 and Sample 2, was distributed in petri dishes and allowed to set; Add with a pipette, 0.1 milliliter (ml) of each sample, for all the dilutions prepared, of the surface of the petri dishes; use a sterilized Drigalsky strap to spread the sample over the surface of the merged medium in the Petri dishes. The cultures were incubated for 48 to 72 hours at 35° C. until the colonies were completely developed, which was generally after 48 to 72 hours, and counted the colonies formed in colonies counter.

Test Results have shown that the primary sludge without the preservative had a bacterial count of 300,000, while the primary sludge having been treated with the current preservative had a bacterial count of 5,000. The current preservative inhibited bacterial growth by reducing the bacterial population hundred fold, compared to the primary sludge without the preservative being added.

Example 2—Measure of the Level of DO

Waste water effluent plants use aeration tanks to suspend microorganisms in wastewater. After leaving the primary treatment stage, sewage is pumped into aeration tanks. The sludge is loaded with microorganisms and mixed with air or pure oxygen. As air is forced into the aeration basins, it increases the activity of these microorganisms and helps keep the organic waste thoroughly mixed. Dissolved oxygen (DO) is added to the aeration basin to enhance the oxidation process by providing oxygen to aerobic microorganisms so they can successfully turn organic wastes into inorganic byproducts or "activated" sludge. Most plants maintain about 1.5 milligrams per liter (mg/L) to about 3.5 mg/L of DO so the microorganisms contained inside the activated sludge can also get oxygen.

A dissolved oxygen sensor, Model 499ADO, from Emerson Process Management, was used in performing the following testing. Oxygen diffuses through the gas-permeable membrane of the sensor and reduced at the cathode. This produced a current between the anode and cathode, which was measured by model 54eA Amperometric Analyzer, manufactured by Emerson Process Management.

The aeration system of the process was monitored for DO level increases or decrease. If suddenly the level of DO increases to more than 3.5 mg/L, without there having been any change in the aeration system, is a sign that the residual preservative in the filtered effluent is affecting the viability of the bacteria in the activated sludge. In the current testing using the preservative, the average DO was 3.0 mg/L, indicating the preservative was not affecting the viability of the bacteria in the activated sludge.

Example 3—Measure of the Level of BOD

Biochemical oxygen demand (BOD) (also called biological oxygen demand) is the amount of dissolved oxygen needed (i. e., demanded) by aerobic biological organisms to break down organic material present in a given water sample at certain temperature over a specific time period. The BOD value is most commonly expressed in milligrams of oxygen consumed per liter of sample during 5 days of incubation (hereinafter referred to as $BOD_5$) at 20° C. and is often used as a surrogate of the degree of organic pollution of water.

The $BOD_5$ can be used as a gauge of the effectiveness of wastewater treatment plants. It is listed as a conventional pollutant in the U.S. Clean Water Act.

Dilution Method

Method 5210B in the Standard Methods for the Examination of Water and Wastewater is a standard method recognized by the U.S. Environmental Protection Agency (EPA). In order to obtain BOD and dissolved oxygen (DO) concentrations in a waste water effluent sample, the sample is measured before and after the incubation period of the sample as prepared above, and appropriately adjusted by the sample corresponding dilution factor (i.e. test tube dilutions 1-6).

The analysis is performed using 300 milliliter (ml) incubation bottles in which buffered dilution water is dosed with seed microorganisms and stored for 5 days in the dark room at 20° C. to prevent DO production via photosynthesis. The dilution of the dissolved oxygen (DO) consumption during sample incubation is typically between 40% and 70% of the initial DO. In addition to the various dilutions of BOD samples, dilution water blanks, glucose glutamic acid (GGA) controls, and seed controls can also be used. The dilution water blank is used to confirm the quality of the dilution water that is used to dilute the other samples. This is necessary because impurities in the dilution water may cause significant alterations in the results. The GGA control is a standardized solution to determine the quality of the seed, where its recommended $BOD_5$ concentration is 198 mg/L±30.5 mg/L. For measurement of carbonaceous BOD (cBOD), a nitrification inhibitor is added after the dilution water has been added to the sample. The inhibitor hinders the oxidation of ammonia nitrogen, which supplies the nitrogenous BOD (nBOD). When performing the $BOD_5$ test, it is conventional practice to measure only cBOD because nitrogenous demand does not reflect the oxygen demand from organic matter. This is because nBOD is generated by the breakdown of proteins, whereas cBOD is produced by the breakdown of organic molecules.

Most pristine rivers will have a 5-day carbonaceous $BOD_5$ below 1 mg/L. Moderately polluted rivers may have a $BOD_5$ value in the range of 2 mg/L to 8 mg/L. Municipal sewage that is efficiently treated by a three-stage treatment process would have a $BOD_5$ value of about 20 mg/L or less.

The BOD was monitored at a facility before and after the addition of the preservative to the system. Testing showed an average BOD of 619 mg/L at the beginning of the waste water treatment process, and was 9 mg/L in the final treated effluent, i.e. a reduction of more than 98% of BOD.

If suddenly the level of BOD in the final effluent became higher than the reference values, it would indicate that the preservative is affecting the viability of the bacteria in the activated sludge, but if the levels of BOD are according to the reference values, this would indicated the preservative is not affecting the bacteria count. When the reduction of BOD is higher than 98%, and the level of BOD in the final effluent is much less than the reference values, indicates the preservative is not affecting the viability of the bacteria in the activated sludge and the treatment in general.

Example 4—Measure of the Level of Nitrogen (Ammonia)

Ammonia nitrogen can be determined directly by colorimetric methods. However, the approved method for wastewater effluent is preliminary distillation of the ammonia into an acid absorbing solution for colorimetric, titrimetric or specific ion electrode determination. If the preliminary distillation step is omitted, comparison data must be available in the laboratory indicating no need for this step.

Standard Method 351.2 of the EPA can be used to measure Total Kjeldahl Nitrogen (TKN), which is an analysis to determine both the organic nitrogen and the ammonia nitrogen contained in a sample of biological sludge. The analysis involves a preliminary digestion to convert the organic nitrogen to ammonia, then distillation of the total ammonia into an acid absorbing solution and determination of the ammonia by an appropriate method, such as the method mentioned above.

Testing was done on the level of total nitrogen in the final effluent of a waste water treatment facility. Acceptable levels must be lower than 30 mg/L, and the level of ammonia nitrogen must be lower than 20 mg/L for discharging into the environment. Testing showed when using the current preservative the average level of ammonia nitrogen in the final treated effluent was at a level of 2.6 mg/L well below the acceptable levels.

If suddenly the level of nitrogen in the final effluent remains higher than the typical values, this indicates that the residual preservative in the filtered effluent is affecting the viability of the bacteria in the activated sludge. If the level of nitrogen is very low, and the level of BDO is low, indicates the level of preservative in the filtered effluent is sufficient. In the current test, the level of ammonia nitrogen was much less than the reference, 2.6 mg/L versus 20 mg/L. The results demonstrate that the current preservative is not affecting the viability of the bacteria in the activated sludge and the waste water treatment in general.

Any references cited in the present application above, including books, patents, published applications, journal articles and other publications, is incorporated herein by reference in its entirety.

We claim:

1. A process for preparing a primary sludge, to be used in the manufacture of cellulosic ethanol, from industrial water effluent, including the step of treating the effluent with a chemical composition comprising benzalkonium chloride; sodium hypochlorite; and oxytetracycline.

2. The process according to claim 1, wherein the solids of the primary sludge comprises at least 20% by weight of cellulosic fiber, can comprise at least 30% by weight fiber and may comprise at least 40% by weight cellulosic fiber.

3. The process according to claim 1, wherein the chemical composition is added to the effluent stream in an amount of from about 100 ppm to about 1,000 ppm.

4. The process according to claim 1, wherein the primary sludge is at least 40% by weight total solids.

5. The process according to claim 1, wherein the amount of benzalkonium chloride relative to the total actives is from 40-75%, the amount of sodium hypochlorite is from 8-20% and the amount of oxytetracycline is from 0.1-1%.

6. The process according to claim 1, wherein the chemical composition is added to the effluent stream prior to a filter press.

7. The process according to claim 1, wherein the chemical composition is added to the industrial effluent stream at the filter press.

8. The process according to claim 1, wherein the bacterial count in the primary sludge is less than 100,000.

9. The process according to claim 1, wherein bio-organism activity in the aeration pond is unaffected by the chemical composition.

10. The process according to claim 1, wherein the industrial effluent stream is from a pulp mill or a pulp and paper mill.

11. A process for preparing cellulosic ethanol comprising preparing a primary sludge from industrial effluent stream, as defined in claim 1, and using the resulting primary sludge in the production of ethanol.

12. The process according to claim 11, wherein the solids of the primary sludge comprises at least 20% by weight cellulosic fiber.

13. A process for preparing a primary sludge, to be used in the manufacture of recycled linerboard, from industrial waste effluent, including the step of treating the effluent with a chemical composition comprising benzalkonium chloride; sodium hypochlorite; and oxytetracycline.

14. The process according to claim 13, wherein the solids of the primary sludge comprises at least 20% by weight cellulosic fiber.

15. The process according to claim 13, wherein the chemical composition is added to the waste effluent stream in an amount of from about 100 ppm to about 1000 ppm.

16. The process according to claim 13, wherein the amount of benzalkonium chloride relative to the total actives is from 40-75%, the amount of sodium hypochlorite is from 8-20% and the amount of oxytetracycline is from 0.1-1%.

17. The process according to claim 13, wherein the chemical composition is added to the industrial effluent stream prior to the filter press.

18. The process according to claim 13, wherein the chemical composition is added to the industrial effluent stream at the filter press.

19. The process according to claim 13, wherein bio-organism activity in the aeration pond is unaffected by the chemical composition.

* * * * *